United States Patent
Kutner et al.

(10) Patent No.: US 7,829,746 B2
(45) Date of Patent: Nov. 9, 2010

(54) PROCESS FOR THE PREPARATION OF CALCIPOTRIOL

(75) Inventors: Andrzej Kutner, Warsaw (PL); Michal Chodynski, Pruszkow (PL); Kinga Leszczynska, Warsaw (PL); Wieslaw Szelejewski, Warsaw (PL); Hanna Fitak, Warsaw (PL)

(73) Assignee: Instytut Farmaceutyczny, Warszawa (PL)

( * ) Notice: Subject to any disclaimer, the term of this patent is extended or adjusted under 35 U.S.C. 154(b) by 0 days.

(21) Appl. No.: 12/685,256

(22) Filed: Jan. 11, 2010

(65) Prior Publication Data

US 2010/0222614 A1 Sep. 2, 2010

Related U.S. Application Data

(63) Continuation of application No. PCT/PL2008/000051, filed on Jul. 11, 2008, and a continuation-in-part of application No. 10/962,873, filed as application No. PCT/PL03/00037 on Apr. 10, 2003.

(30) Foreign Application Priority Data

Apr. 11, 2002 (PL) .................... 353328
May 12, 2002 (PL) .................... 353832
Jul. 12, 2007 (PL) .................... 382912

(51) Int. Cl.
*C07C 35/00* (2006.01)

(52) U.S. Cl. .................... 568/819

(58) Field of Classification Search .................... 568/819
See application file for complete search history.

(56) References Cited

U.S. PATENT DOCUMENTS

2005/0119241 A1* 6/2005 Kutner et al. .............. 514/167

FOREIGN PATENT DOCUMENTS

WO   WO99/36400     *   7/1999
WO   03/087048 A2       10/2003

OTHER PUBLICATIONS

Publisher: Wydawnictwo Czasopism i Ksiazek Technicznych SIGMA-NOT Sp. z o.o., Autor: Michal Chodynski et al., Title: Modification of a new for method manufacturing calcipotriol, pp. 760-763, Date of publication: Aug. 2007, Place of publication: Warszawa, Poland.

* cited by examiner

*Primary Examiner*—Sikarl A Witherspoon
(74) *Attorney, Agent, or Firm*—Matthias Scholl, PC; Matthias Scholl

(57) ABSTRACT

A process for the preparation of calcipotriol at least including: (a) reacting a C-22 phenylsulfonyl derivative of cholecalciferol of Formula 2, wherein $R_1$ and $R_2$ are the same or different and represent hydroxyl protecting groups, with a silyl derivative of alfa-hydroxy aldehyde of Formula 3, wherein $R_3$ represents silyl group of formula $Si(R_4)(R_5)(R_6)$, where $R_4$-$R_6$ are the same or different and represent $C_{1-6}$ alkyl or phenyl groups, in the presence of a strong organic base in an aprotic solvent, followed by reductive desulfonation of the obtained diastereomeric mixture of alfa-hydroxysulfones with sodium amalgam, removal of the hydroxyl protecting groups, and purification of the product. The process leads to the formation of calcipotriol containing less than 0.3% of the (22Z)-isomer. The obtained calcipotriol is free of mercury traces.

11 Claims, 1 Drawing Sheet

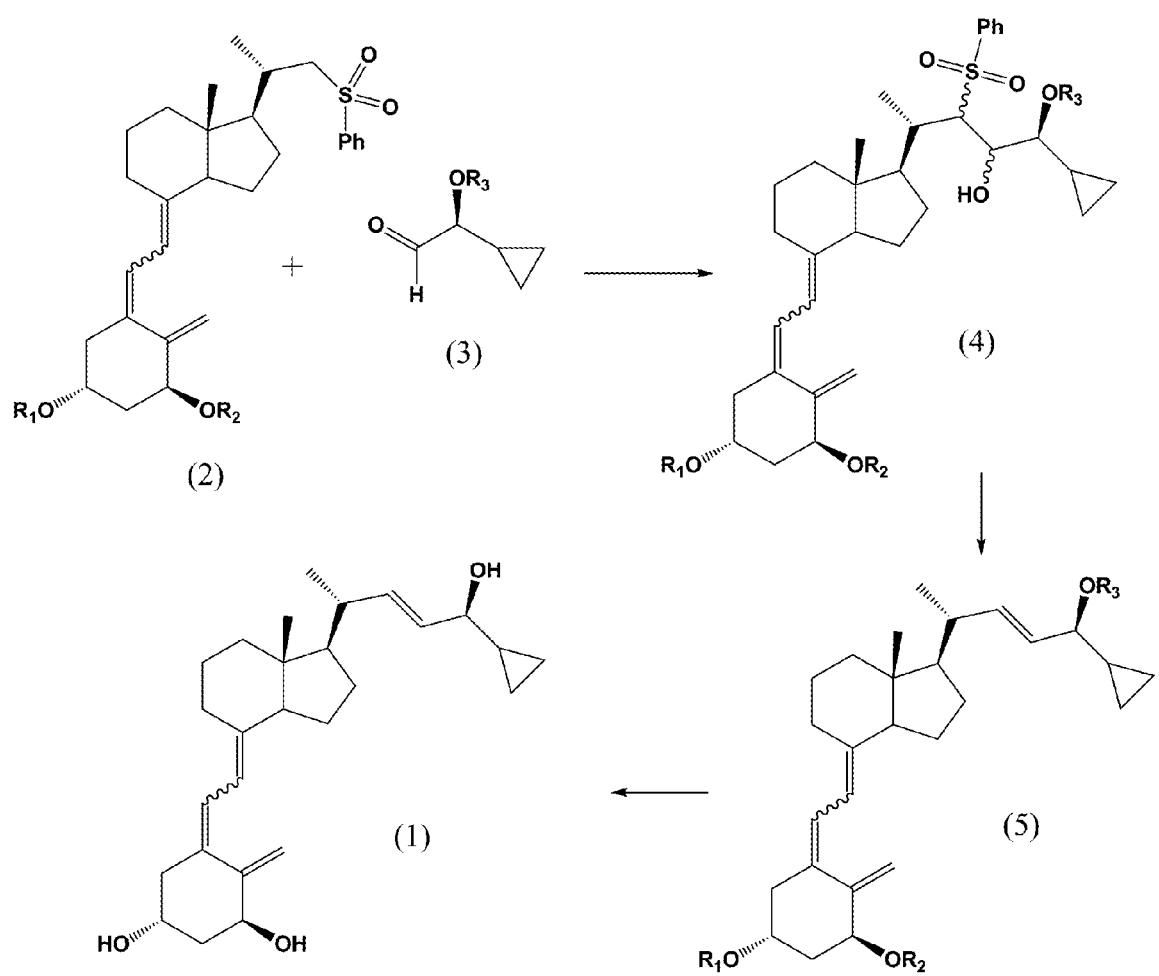

US 7,829,746 B2

PROCESS FOR THE PREPARATION OF CALCIPOTRIOL

CROSS-REFERENCE TO RELATED APPLICATIONS

This is a continuation of International Patent Application No. PCT/PL2008/000051, with an international filing date of Jul. 11, 2008, and claims priority benefits to Polish Patent Application No. P-382912, filed Jul. 12, 2007. The contents of these specifications including any intervening amendments thereto are incorporated herein by reference. In addition, this is a continuation in part of U.S. application Ser. No. 10/962,873, filed on Oct. 8, 2004, now pending, which is a national phase application of International Patent Application No. PCT/PL2003/000037, with an international filing date of Apr. 10, 2003, designating the United States, now pending, which is based upon Polish Application No. 353328 filed on Apr. 11, 2002 and Polish Application No. 353832 filed on May 12, 2002.

BACKGROUND OF THE INVENTION

1. Field of the Invention

This invention relates to a process for preparation of cholecalciferol derivatives having a double bond in the side chain, particularly calcipotriol (calcipotriene).

2. Description of the Related Art

Calcipotriol, (1α,3β,5Z,7E,22E,24S)-24-cyclopropyl-9,10-secochola-5,7,10(19),22-tetraene-1,3,24-triol, is a synthetic vitamin D3 analogue. It exhibits antiproliferative activity and is useful in the treatment of psoriasis.

There are several known methods for the preparation of calcipotriol. The preparation method developed by Calverley (WO 87/00934; Tetrahedron 43, 4609 (1987)), is based on a Wittig reaction of C-22 aldehyde derivative of cholecalciferol, having a triene (5E,7E) configuration, with triphenylphosphorane cyclopropyl ketone glide. The reduction of the side chain carbonyl group to C-24 alcohol, gives a mixture of C-24 diastereomers. The disadvantage of this process is the formation of triphenylphosphine oxide as a side product which is water insoluble and difficult to remove from the reaction mixture. The desired (24S)-alcohol must separated by column chromatography, which leads to a loss of over a half of the obtained product. As a consequence, the undesired product, i.e., the (5E,24S) isomer, is subjected to photoisomerization to yield the product of a proper (5Z),(24S) configuration.

WO 2005/095336 employs the more reactive phosphonate derivative instead of triphenylphosphorane in a Wittig-Horner reaction. A phosphate ester formed in the reaction is soluble in water, unlike the triphenylphosphine oxide, and thus can be easily removed from the reaction mixture. Despite this improvement, the disadvantages of Calverley's synthetic pathway still remain and it is necessary to separate C-24 diastereomers in the last step.

Another method for preparing calcipotriol (Synlett, 1990, 157) relies on condensing C-22-seleneacetal with a fragment of the side chain, namely, (S)-2-((tert-butyl)dimethyl)silyloxy-2-cyclopropylacetyl aldehyde, resulting in the formation of a mixture of diastereoisomeric 23-hydroxy-22-methylselenides. These are treated with methanesulfoneyl chloride and triethylamine. In the two following steps, hydroxyl and selenemethyl groups are removed, resulting in the formation of a mixture of (5E),(22E/Z) olefins as their protected triols. The mixture is chromatographically separated and the obtained product of (5E),(22E) configuration is subjected to anthracene-sensitized photoisomerization of (5E,7E)-triene to (5Z,7E)-triene, followed by the removal of the silyl groups. On account of some drawbacks concerning work with seleneorganic compounds (unpleasant odor, toxicity and low stability of methylselenol), and lack of stereoselectivity during selenium removal from (α-hydroxy)methylselenides, this method is not suitable in a large scale production.

Another way of obtaining calcipotriol, accompanied by its C-24 epimer, is disclosed in JP 08325226. This method is based on coupling of two synthons: calcipotriol A ring -(4R,6S)-4,6-di(t-butyl)dimethylsilyloxy-7-octen-1-yne and a 7-bromo derivative consisting of calcipotriol CD rings, under Heck reaction conditions. The coupling is followed by removal of protecting groups. The synthesis of both synthons used in the coupling-cyclization reaction proved to be a difficult multistep process.

In JP 06316558 disclosed is the preparation of (7Z)-calcipotriol isomer from appropriately substituted cholesta-5,7-diene in a photochemical or thermal rearrangement process.

The prior art methods for the preparation of calcipotriol have certain disadvantages connected with easy isomerization of the asymmetric center at C-20 of the starting C-22 aldehydes, lack of selectivity during C-24 ketone reduction and the necessity for use of preparative chromatography during purification step. These factors adversely affect the implementation of the described syntheses in routine laboratory practice.

A number of methods were developed to increase the total yield of calcipotriol synthesis, whereas undesired (24R)-isomer is transformed into the mixture enriched with the desired (24S) epimer. In WO 03/106412, the method of regaining the desired calcipotriol (24S) epimer is disclosed. The process is based on the racemization of calcipotriol C-24 p-nitrobenzoate under Mitsunobu reaction conditions using diisopropyl azadicarboxylate.

In WO 2006/024296 in turn, the epimerization of C-24 alcohol in aqueous organic medium under acidic conditions is disclosed. In this process no additional hydroxyl group transformation is necessary. Although this procedure is superior to the one described in WO 03/106412 as the esterification as well as alcohol hydrolysis are avoided, the problems with diastereomer separation and with the inability to isolate over half of the obtained racemic mixture still exist.

Some attempts were undertaken towards calcipotriol preparation in direct olefination method under Julia-Kocienski protocol, known in the art (P. R. Blakemore at al., Synlett, 26 (1998); P. R. Blakemore at al., J. Chem. Soc., Perkin Trans. I, 955 (1999)), applying a phenyltetrazole sulfone. This method was applied in the synthesis of cholecalciferol derivatives (Kutner, A., Przem. Chem., 85(5), 322 (2006)). The attempts to overcome the difficulties with low transformation rate of thiophenyltetrazole derivative into appropriate sulfonylphenyltetrazole have failed. In addition, the high cost of commercially available main reagent, 1-phenyltetrazole-5-thiol, may be limiting in the implementation of this method in the production scale.

In WO 03/087048 disclosed is a method of calcipotriol preparation using benzothiazole sulfone. Use of benzothiazole sulfone was first reported for the direct aldehydes olefination by Sylvestre Julia (J. B. Baudin at al., Tetrahedron Lett. 32, 1175 (1991)). In the Julia olefination, condensation of deprotonated benzothiazole sulfone and aldehyde under basic conditions proceeds, followed by subsequent cyclization and rearrangement, accompanied by sulfur dioxide elimination. As a reaction result, olefin is formed as well as a water soluble benzothiazolone salt (J. B. Baudin at al., Bull. Soc. Chim. Fr. 130, 336 (1993); Bull. Soc. Chim. Fr. 130, 856 (19930).

Oxidation of benzothiazole sulfide to sulfone, unlike phenyltetrazole sulfide, proceeds in moderate yield (62%). Crystalline C-22 sulfonyl benzothiazole derivative is a convenient, advanced intermediate in the synthesis of calcipotriol. However, under the reaction conditions with the use of benzothiazole sulfone, (22Z) by-product is formed in over 10% yield. The removal of this by-product up to the pharmaceutically accepted level is accomplished in a multi-step crystallization process. The elaborate purification procedure affects the total yield of the synthetic process.

In the art, Marc Julia's (M. Julia, J. M. Paris, Tetrahedron Lett. 1973, 4833) olefination method was one of most frequently used, when C=C double bond formation in a molecule was necessary. In this process aldehyde reacted with phenyl sulfonyl anion, generated in situ when treated with n-butyl lithium; obtained intermediate was subsequently functionalized and subject to reductive elimination with sodium amalgam to yield alkene.

Regardless of the popularity of this method, it has not been applied in direct condensation of cholecalciferol C-22 phenylsulfonyl derivative, having methyl group at the alfa position in respect to the phenylsulfonyl substituent, and aliphatic aldehyde having at alfa position bulky substituent, such as tert-butyl-diphenylsilyl. In light of WO 03/087048, that type of hydroxyl protection facilitates purification and isolation of the reaction product. The silyl protection also enables the starting aldehyde detection by UV spectroscopy in TLC and HPLC chromatography, and causes the increase of molecular density and decrease of volatility thereof.

BRIEF SUMMARY OF THE INVENTION

Now, it has unexpectedly been found that cholecalciferol C-22 phenylsulfonyl derivative of Formula 2 reacts in good yield with alfa-hydroxy aldehyde of Formula 3, the side chain precursor bearing bulky silyl substituent, in a condensation reaction under the Julia protocol.

The invention provides the process for preparation of calcipotriol,

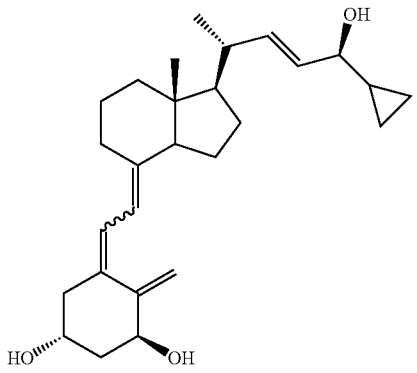

Calcipotriol comprising the steps of:
(a) reacting a C-22 phenylsulfonyl derivative of cholecalciferol of Formula 2,

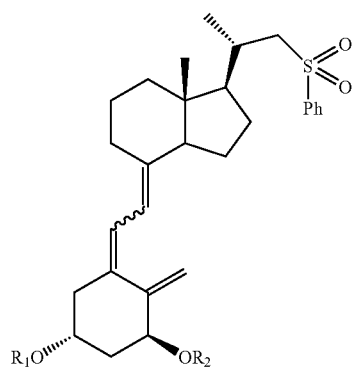

Formula 2 wherein $R_1$ and $R_2$ are the same or different and represent hydroxyl protecting groups, with a silyl derivative of alfa-hydroxy aldehyde of Formula 3,

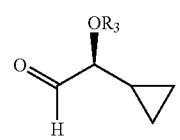

Formula 3 wherein $R_3$ represents silyl group of formula $Si(R_4)(R_5)(R_6)$, where $R_4$-$R_6$ are the same or different and represent $C_{1-6}$ alkyl or phenyl groups, in the presence of a strong organic base in an aprotic solvent, to yield a diastereomeric mixture of alfa-hydroxysulfones of Formula 4,

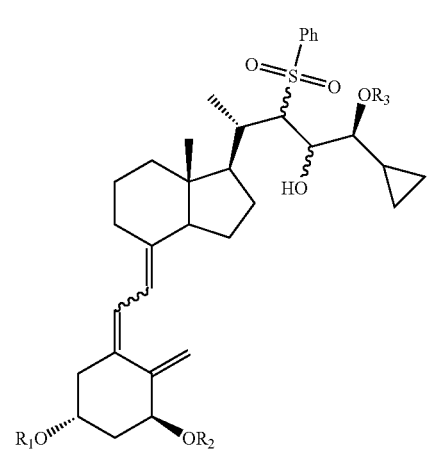

Formula 4 wherein the substituents $R_1$-$R_3$ are as defined above;
(b) performing reductive desulfonation of alfa-hydroxysulfones of the Formula 4 obtained in step (a) with sodium amalgam, to yield the olefination product of Formula 5,

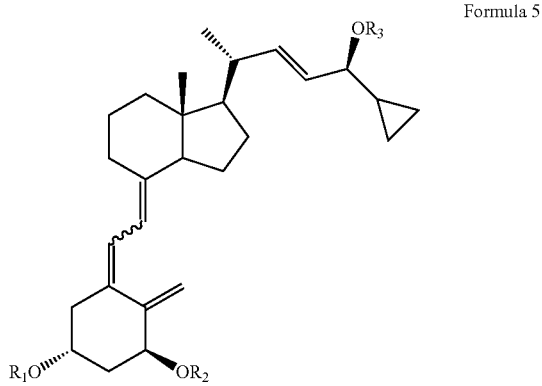

Formula 5

(c) removing the hydroxyl protecting groups under standard conditions to obtain calcipotriol, and
(d) purifying the calcipotriol obtained in (c).

As the strong organic base, organometallic compounds, such as lithium, sodium or potassium organic derivatives, and preferably n-butyl lithium, are used.

As the aprotic solvents, phosphoric acid alkyl amides or urea alkyl derivatives, preferably hexamethylphosphorous triamide (HMPT) or tetrahydrofurane (THF), are used.

The hydroxyl protecting group in the phenylsulfone of Formula 2 is any group routinely used in vitamin D chemistry, such as for example acyl, alkylsilyl or alkoxyalkyl group. Acyl group includes alkanoyl and carboxyalkanoyl groups, having 1-6 carbon atoms, preferably the acetyl group. Usual alkoxyalkyl groups are methoxymethyl, ethoxyethyl, tetrahydrofuranyl and tetrahydropyranyl groups. Most common silyl groups are trialkylsilyl, dialkylarylsilyl, alkyldiarylsilyl, triarylsilyl group, such as for example trimethylsilyl, triethylsilyl, t-butyl-dimethylsilyl, triphenylsilyl group.

In the preferred embodiment of the invention, the hydroxyl groups in both reagents are protected with the same silyl substituents, e.g., t-butyldimethylsilyloxy groups.

Deprotection of hydroxyl groups is carried out under basic conditions. Usually used silyl groups are removed when treated with tetrabutylammonium fluoride, in organic solvents such as THF or acetone, often in the presence of water.

5 or 10% sodium amalgam used in the dehydroxy-desulfonation reaction is commercially available.

The starting compound, C-22 phenylsulfone of Formula 2, is the key synthon used in vitamin D chemistry. It is a crystalline compound of high stability, that enables its easy purification to required pharmaceutical purity before is being reacted with an aldehyde.

The process according to the invention enables a successful preparation of calcipotriol in a direct chemical synthesis, avoiding separation of the diastereomeric mixture. The results of chromatography with chiral stationary phase proved that the amount of undesired (22Z)-isomer reached only 2.2% in a crude reaction mixture. The contents of this impurity can be reduced to below 0.3% during one or two crystallizations.

Unexpectedly, it has been discovered that the product obtained by the process of the invention and subsequently purified by standard procedure, such as the column chromatography and crystallization, is free of mercury. The traces of mercury were not detected, even using very sensitive analytical methods, such as atomic absorption method.

BRIEF DESCRIPTION OF THE DRAWINGS

The single FIGURE illustrates a process for the preparation of calcipotriol according to one embodiment of the invention.

DETAILED DESCRIPTION OF THE INVENTION

The invention is illustrated by the following examples, which should not be construed as any limitation of its scope.

EXAMPLES

Example 1

(5Z,7E)-(1S,3R,24S)-1,3-bis(t-butyldimethylsilyloxy)-(22R,23R/22R,23S/22S,23R/22S,23S)-22-sulfonylphenyl-23-hydroxy-24-cyclopropyl-24-t-butyldiphenylsilyloxy-9,10-secochola-5,7,10(19)-trienes (4)

(5Z,7E)-(1S,3R)-1,3-bis(t-butyldimethylsilyloxy)-22-sulfonylphenyl-23,24-dinor-9,10-secochola-5,7,10(19)-triene (Formula 2, $R_1=R_2=$TBDMS) (384 mg, 0.55 mmol) was dissolved in THF (2 mL). The flask was placed in a cooling bath (−68° C.) on a magnetic stirrer under Ar. While stirring, n-butyl lithium (1.6 M in THF, 350 μL, 0.56 mmol)) was added drop-wise with a syringe. Stirring was continued for 30 min. at −68° C. Next, (2S)-2,2-cyclopropyl-t-butyldiphenylsilyloxyetanal (Formula 3, $R_3=$TBDPS) (200 mg, 0.59 mmol) was slowly added drop-wise. Cooling bath was removed after 30 min. and the reaction mixture was stirred for additional 2 h. at ambient temp. Brine (1 mL) was added, organic phase was separated and dried over $Na_2SO_4$ (100 mg). After filtration, solvents were removed under reduced pressure. The residue was filtered through silica gel (2 g). The mixture of crude products (5Z,7E)-(1S,3R,24S)-1,3-bis(t-butyldimethylsilyloxy)-(22R,23R/22R,23S/22S,23R/22S,23S)-22-sulfonylphenyl-23-hydroxy-24-cyclopropyl-24-t-butyldiphenylsilyloxy-9,10-secochola-5,7,10(19)-trienes (Formula 4, $R_1=R_2=$TBDMS, $R_3=$TBDPS) (500 mg, 88%) was obtained, as colorless powder.

Example 2

(5Z,7E,22E)-(1S,3R,24S)-1,3-bis(t-butyldimethylsilyloxy)-24-cyclopropyl-24-t-butyldiphenylsilyloxy-9,10-secochola-5,7,10(19),22-tetraen (5)

The mixture of (5Z,7E)-(1S,3R,24S)-1,3-bis(t-butyldimethylsilyloxy)-(22R,23R/22R,23S/22S,23R/22S,23S)-22-sulfonylphenyl-23-hydroxy-24-cyclopropyl-24-t-butyldiphenylsilyloxy-9,10-secochola-5,7,10(19)-trienes (Formula 4, $R_1=R_2=$TBDMS, $R_3=$TBDPS) (500 mg, 0.45 mmol) was dissolved in THF (1 mL), in a round-bottom flask of 10 mL capacity. The flask was placed on a magnetic stirrer and saturated methanolic $Na_2HPO_4$ solution (2 mL), followed by sodium amalgam Na/Hg (1.2 g) were added. The reaction mixture was vigorously stirred at ambient temp. for 2 h. The solution was decanted and the solvents were removed under reduced pressure. The product was extracted with hexane (3×5 mL) from dry residue. Hexane was evaporated and the residue was filtered through silica gel (2 g). (5Z,7E,22E)-(1S,3R,24S)-1,3-bis(t-butyldimethyldimethylsilyloxy)-24-cyclopropyl-24-t-butyldiphenylsilyloxy-9,10-secochola-5,7,10(19),22-tetraene (Formula 5, $R_1=R_2$=TBDMS, $R_3$=TBDPS) was obtained (276 mg, 64%), as colorless powder.

Example 3

(5Z,7E,22E)-(1S,3R,24S)-24-cyclopropyl-9,10-secochola-5,7,10(19),22-tetraen-1,3,24-triol (1)

(5Z,7E,22E)-(1S,3R,24S)-1,3-bis(t-butyldimethylsilyloxy)-24-cyclopropyl-24-t-butyldiphenylsilyloxy-9,10-secochola-5,7,10(19),22-tetraene (Formula 5, ($R_1=R_2$=TBDMS, $R_3$=TBDPS) (276 mg, 031 mmol) was dissolved in THF (2 mL) under Ar. The solution was warmed in a heating bath (+60° C.) on a magnetic stirrer. Tetrabutylammonium fluoride solution (1 M in THF, 1.0 mL, 1.0 mmol) was added drop-wise and stirring was continued for 1.5 h (+60° C.). After removal of a heating bath, the solution was cooled down to 20° C. and 1 mL of brine was added. Organic phase was separated, dried over $Na_2SO_4$ (200 mg), filtered and condensed under the vacuum. The crude product was contaminated with 2.2% of (22Z)-isomer of calcipotriol (HPLC). The residue was filtered through silica gel (2 g). After removal of solvents, the resulting solid was crystallized from ethyl acetate (500 μL). (5Z,7E,22E)-(1S,3R,24S)-24-cyclopropyl-9,10-secochola-5,7,10(19),22-tetraen-1,3,24-triol of Formula 1 was obtained (89 mg, 68%), as colorless crystals, of 98.5% purity (HPLC), UV $\lambda_{max}$ (EtOH) 265.0, 212.0 nm, $\lambda_{min}$ 229.0 nm; IR ν 3401, 2949, 2927, 2869, 1631, 1432, 1376, 1325, 1246, 1064, 981, 911, 797 cm$^{-1}$; $^1$H-NMR (δ, ppm): 0.57 (3H, s, 18-$CH_3$), 1.04 (3H, d, J=8 Hz, 21-$CH_3$), 3.42 (1H, m, 24-H), 4.23 (1H, m, 3-H), 4.43 (1H, m, 1-H), 5.00 (1H, bs, 19Z-H), 5.35 (1H, bs, 19E-H), 5.50 (2H, m, 22-H and 23-H), 6.01 (1H, d=11.2 Hz, 7-H), 6.38 (1H, d=11.2 Hz, 6-H). 0.3% of the (22Z)-isomer was detected.

This invention is not to be limited to the specific embodiments disclosed herein and modifications for various applications and other embodiments are intended to be included within the scope of the appended claims. While this invention has been described in connection with particular examples thereof, the true scope of the invention should not be so limited since other modifications will become apparent to the skilled practitioner upon a study of the drawings, specification, and following claims.

All publications and patent applications mentioned in this specification are indicative of the level of skill of those skilled in the art to which this invention pertains. All publications and patent applications mentioned in this specification are herein incorporated by reference to the same extent as if each individual publication or patent application mentioned in this specification was specifically and individually indicated to be incorporated by reference.

The invention claimed is:

1. A process for the preparation of a compound of the following formula

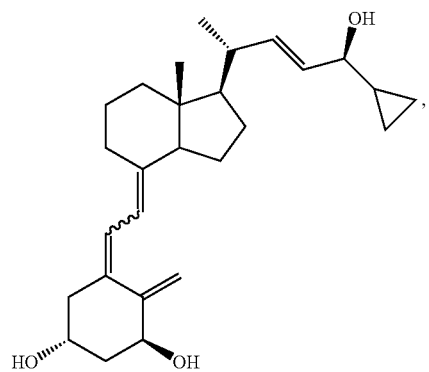

the process comprising:
(a) reacting in the presence of a strong organic base in an aprotic solvent, a compound of the following formula:

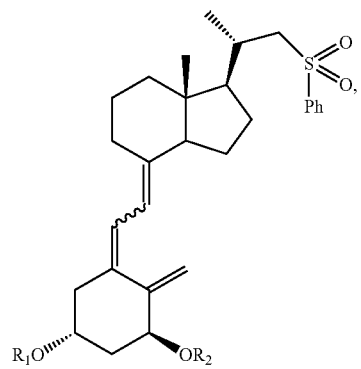

wherein $R_1$ and $R_2$ are the same or different and independently represent hydroxyl protecting groups,
with a compound of the following formula:

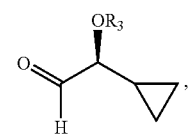

wherein $R_3$ represents a silyl group of formula $Si(R_4)(R_5)(R_6)$, where $R_4$, $R_5$ and $R_6$ are the same or different and independently represent $C_{1-6}$ alkyl or phenyl groups,
to yield a diastereomeric mixture of compounds of the following formula:

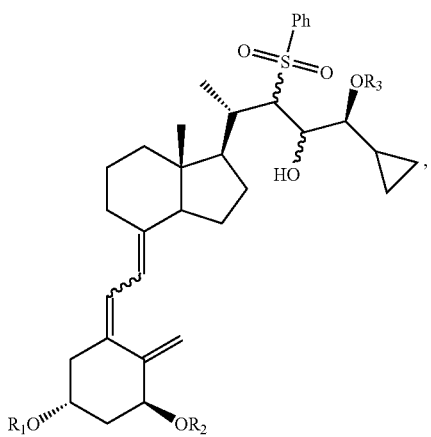

wherein $R_1$, $R_2$, and $R_3$ are as defined above;

(b) performing reductive desulfonation of the diastereomeric mixture of compounds obtained in (a) using sodium amalgam to yield a compound of the following formula:

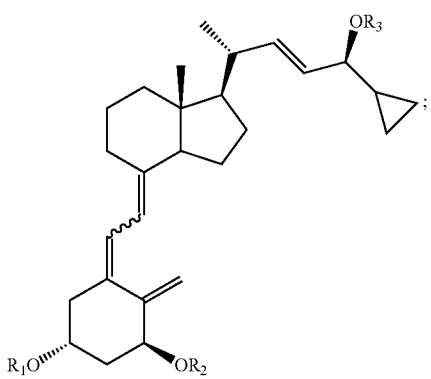

and (c) removing the hydroxyl protecting groups, $R_1$, $R_2$, and $R_3$, to yield the compound of the following formula:

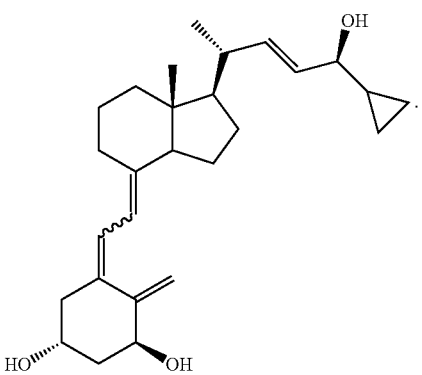

2. The process of claim 1, further comprising purifying the product obtained in step (c) to yield purified product.

3. The process of claim 1, wherein $R_1$, $R_2$ and $R_3$ each independently represent t-butyldimethylsilyloxy group.

4. The process of claim 1, wherein the product obtained in (c) contains less than 2.2% w/w of the (22Z)-isomer.

5. The process of claim 1, further comprising purifying the product obtained in (c) by column chromatography followed by crystallization to yield purified product.

6. The process of claim 2, wherein said purified product contains less than 0.3% w/w of the (22Z)-isomer.

7. The process of claim 5, wherein said purified product contains less than 0.3% w/w of the (22Z)-isomer.

8. The process of claim 2, wherein said purified product is free of mercury.

9. The process of claim 5, wherein said purified product is free of mercury.

10. The process of claim 1, wherein said strong organic base is n-butyl lithium.

11. The process of claim 1, wherein said aprotic solvent is tetrahydrofurane.

\* \* \* \* \*